United States Patent [19]

Zelagin et al.

[11] 4,155,711
[45] May 22, 1979

[54] METHOD AND APPARATUS FOR DETERMINING THYROID FUNCTION OF MULTIPLE SAMPLES

[76] Inventors: Michael Zelagin, 523B R.D. #1, Jackson, N.J. 08527; Raymond A. Smutko, 233 K Ct., Seaside Park, N.J. 08752

[21] Appl. No.: 589,688

[22] Filed: Jun. 24, 1975

[51] Int. Cl.² .......................................... G01N 33/16
[52] U.S. Cl. .............................. 23/230.6; 23/230 B; 424/1; 422/65; 422/71; 422/100
[58] Field of Search ............... 23/230 B, 230.3, 230.6; 424/1, 12; 195/103 A

[56] References Cited

U.S. PATENT DOCUMENTS

| | | | |
|---|---|---|---|
| 3,414,383 | 12/1968 | Murphy | 23/230.6 |
| 3,451,777 | 6/1969 | DiGiulio | 23/230.6 |
| 3,519,390 | 7/1970 | Dickey et al. | 23/230.6 |
| 3,620,681 | 11/1971 | Wright | 23/259 X |
| 3,710,117 | 1/1973 | Gross et al. | 23/230.6 |
| 3,711,247 | 1/1973 | Adams | 23/230.6 |
| 3,721,528 | 3/1973 | Mead et al. | 23/230.6 |
| 3,743,482 | 7/1973 | Eisentraut | 23/230.6 |
| 3,754,863 | 8/1973 | Reunanen | 23/230.6 |
| 3,850,577 | 11/1974 | Ashkar | 23/230.6 |
| 3,881,872 | 5/1975 | Naono | 23/253 R |
| 3,951,605 | 4/1976 | Natelson | 23/253 R |

OTHER PUBLICATIONS

Sekadde et al., "Rapid Radioimmunoassay of Triiodothyronine", Clin. Chem., vol. 19, No. 9, pp. 1016–1021 (1973).

Primary Examiner—R. E. Serwin

[57] ABSTRACT

A method and apparatus for measuring thyroid function by means of measuring the up-take of a radioactive tracer on a resin involves causing the mixing of resin with tracer for predetermined periods and preferably by a means which causes agitation of the resin in the tracer-containing sample to be tested. Also disclosed is an apparatus useful for handling multiple samples to be tested.

9 Claims, 4 Drawing Figures

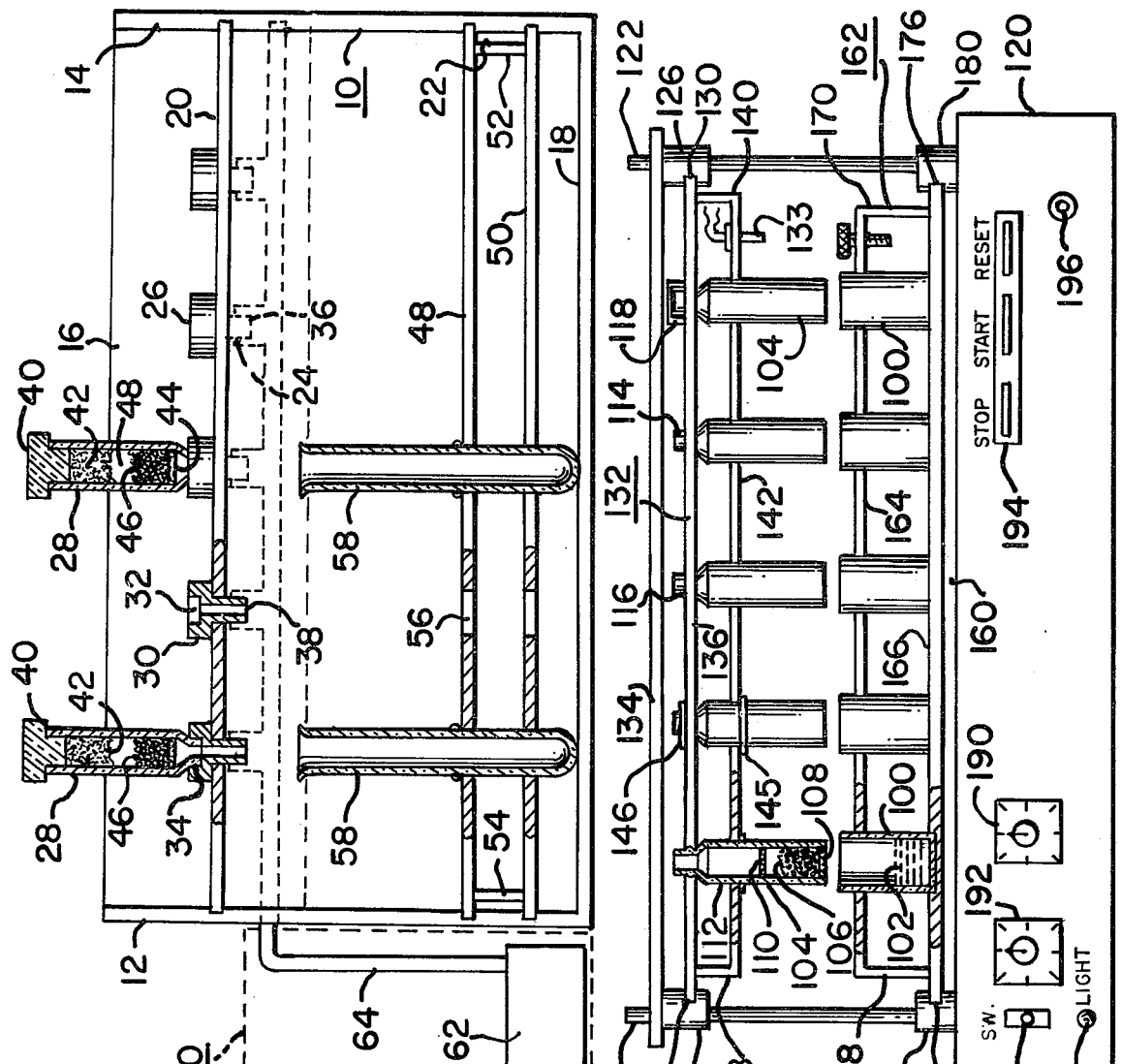

METHOD AND APPARATUS FOR DETERMINING THYROID FUNCTION OF MULTIPLE SAMPLES

BACKGROUND OF THE INVENTION

This invention relates generally to the field of body fluid analysis and more particularly to an improved method and apparatus for analyzing multiple samples, in-vitro, utilizing radioactive tracers to determine relative resin binding of the constituent to be determined.

An application of the invention relates to an improved method and apparatus for determining the thyroid hormone content of blood. Thyroid hormones, such as triiodothyronine, or $T_3$ as it is commonly known, are produced in the thyroid gland and are carried in the blood to the body cells where the hormones ultimately produce their well-known metabolic effects. The thyroid hormones regulate the activity of human cells in carrying out the particular functions of these cells. Consequently, when the thyroid gland puts out an excess of these hormones, these body cells are overactive, the body burns up excess food and the patient has the condition known as hyperthyroidism. In hyperthyroidism, the reverse situation caused by a deficiency of thyroid hormones takes place.

It is well known that the thyroid hormones do not exist freely in large amounts in the plasma but are bound to specific protein fractions of that tissue. In this bound form, the hormones are transported throughout the body. The thyroid hormones are specifically bound to two distinct plasma proteins, thyroxine binding globulin (TBG) and prealbumen, which are normally present in such low concentrations as to defy analysis by conventional methods. Nevertheless, the binding strength or capability of the protein fractions to bind the thyroid hormones and the quantity of binding proteins available has been shown to be generally constant within narrow limits in various blood samples from most humans.

It is also well known that certain resins also have the ability to bind the thyroid hormones. In other words, these resins have an affinity for the thyroid hormones so that in the presence of these well known resins, a fraction of the thyroid hormones becomes bound to the resins even in the presence of serum proteins. The magnitude of this fraction is influenced primarily by the quantity of thyroid hormone in the blood when the binding capacity of thyroxine binding proteins is within normal limits. Consequently, it has been the practice to test indirectly for the thyroid hormone content of blood by contacting the blood with a radioactive thyroid hormone, and a quantity of a resin having an affinity for the thyroid hormone. In the case of a hyperthyroid, in which the thyroid gland of the patient was overactive, the protein fraction in the serum approaches saturation with thyroid hormones. Consequently, the resin attracts and binds a large proportion of the radioactive thyroid hormone. The extent to which the resin takes up radioactive hormone from the blood sample is an indirect measure of the thyroid hormone content of the blood sample. This measurement is sometimes simply stated at "$T_3$ resin uptake," so in hyperthyroidism there is a high $T_3$ resin uptake. In a hyperthyroid situation, the amount of thyroid hormone present in the patient's serum is reduced so that the serum proteins are "starved" for hormones. As a result, more of the added radioactive hormone will be bound to plasma proteins and less to the resin having an affinity for the hormone. Consequently, the test, in such a situation, will show a lesser take-up of hormone by the resin, i.e., a low $T_3$ resin uptake.

In carrying out the above test, the usual procedure is to obtain serum from the patient, place this serum in a test tube or glass vial, add a predetermined amount of resin to the vial, and then add radioactive $T_3$ to the serum-resin mixture. In one method the $T_3$ is added directly to the resin. The radioactivity of this mixture is recorded and then the mixture is incubated for a period of time between thirty minutes and two hours. In many methods agitation or mixing is required during this incubation period. After the incubation period, the resin must be separated from the serum, following which the amount of radioactive material bound to either the serum alone or the resin alone is determined by making another radioactivity recording. This separation is generally accomplished by allowing the resin to settle (by centrifugation or by gravity) and either (a) withdrawing a known fraction of the overlying serum, or (b) washing the settled resin by adding several volumes of water decanting the water-serum mixture after each addition of water. The long incubation period with agitation was thought to be necessary for accurate analysis since that represented the approximate time for the system to reach equilibrium and the resin to absorb the maximum possible amount of hormone.

Similarly, Murphy and Pettee described a procedure for the determination of $T_4$ as thyroxine by competitive protein-binding analysis utilizing radioactive thyroxine which is allowed to interact with the patient's serum in the presence of a stabilizing agent and then separating the unbound thyroxine from the bound thyroxine by means of an ion exchange resin which competes for the thyroxine with the thyroxine binding globulin (TBG) of the blood. Still another method is described for $T_3$ analysis in U.S. Pat. No. 3,451,777, wherein an excess of resin is used in a fixed, packed column, which is washed by forcing a wash fluid through the column which has been contacted with a sample-radioactive $T_3$ mixture.

The purpose of this invention is to provide a method which enables good precision, sensitivity and range of reportable value, while, in addition, providing a method and device which will markedly aid patient testing by enabling multiple samples and controls to be processed for analysis at essentially the same time, for shorter periods of time, and in a time controlled manner.

SUMMARY OF THE INVENTION

A method for determining an index of a constituent of body fluid comprises the steps of:

(1) adding a known quantity of a radioactive tracer to an aliquot of the sample of body fluid to be measured in a sample container;

(2) mixing the radioactive tracer-sample aliquot in the container to attain a uniform equilibrated solution;

(3) contacting the equilibrated solution with a resin having an affinity for said tracer in a manner so as to cause agitation of the resin in the solution for a predetermined controlled period of time which is substantially less than the time required for equilibrium of the system to be reached;

(4) determining the amount of radioactivity bound by the resin (the radioactive resin up-take); and (5) comparing said uptake with control standards run in a similar manner for the same time periods to obtain quantitative analysis of said sample.

The apparatus useful for the analysis of multiple samples of body fluid includes a vial rack for holding a plurality of vials, a plurality of vials containing a loosely packed resin column, means through which a sample solution containing radioactive tracer can be added to said resin vials in a manner causing agitation of said resin and means for controlling the contact time of each of said sample solutions with said resin to a predetermined time which is equal for all samples, said time being substantially less than the equilibrium time for saturation of said resin with said radioactive tracer.

BRIEF DESCRIPTION OF THE DRAWINGS

The invention will be described with reference to the analysis of $T_3$; however, it should be understood that the method and apparatus of the invention can be used in the analysis of other constituents of body fluids.

FIG. 1 is a front elevational, partially cross-sectional view of a novel apparatus embodying the invention;

FIG. 2 is a front elevational view of an automated apparatus embodying the invention;

DETAILED DESCRIPTION OF THE INVENTION

Figure 3:
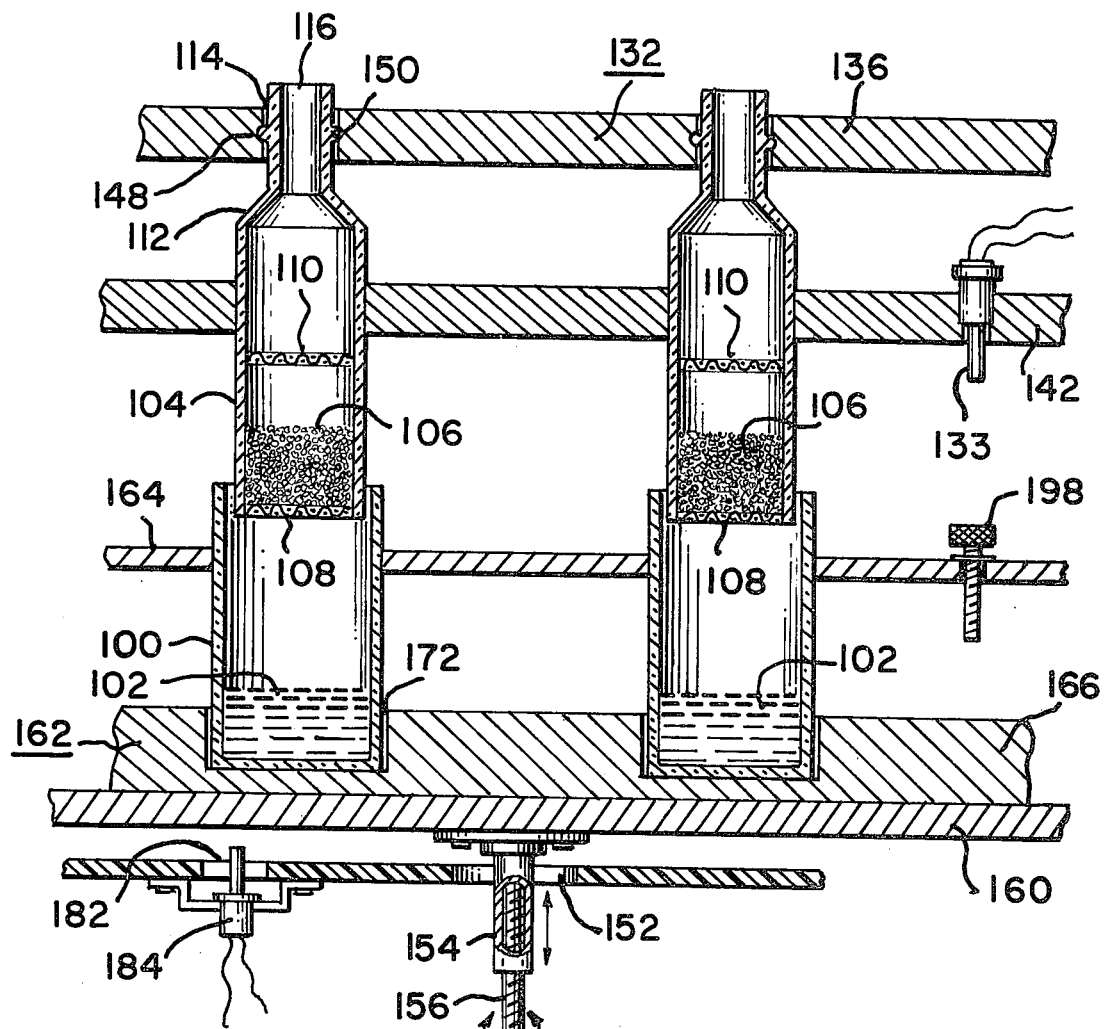
FIG. 3 is a side, cut-away partially schematic representation of the apparatus shown in FIG. 2.

Referring to FIG. 1, there is shown a novel apparatus useful in the radioactive uptake analysis of multiple samples of body fluid. The apparatus comprises a support frame 10 having side members 12 and 14, a back member 16 and a bottom member 18. Side members 12 and 14 are each slotted from front to back in three places as shown so as to accommodate a removable sample vial rack 20 and a removable eluent vial rack 22. The vial rack 20 and eluent rack 22 are slidably mounted in the respective slots of the side members 12 and 14. Sample vial rack 20 contains a plurality of spaced circular holes 24 therethrough, generally forming rows and columns. Inserted in each of these holes is a flow rate control plug 26. The flow rate control plug is the means employed for controlling the flow rate of fluid from sample vials 28 which are inserted in the top of the plug 26. The flow rate control plug 26 is a simple device, preferably made of a plastic material which can be precision bored. It has a wide, flat head, top portion 30 which is formed with a relatively wide hole 32 therein. The width of hole 32 is such as to snugly accommodate the lower end 34 of sample vial 28 so as to support the vial 28 in an upright position. The top portion 30 of the plug 26 rests on the top surface of the sample rack 20. A narrow neck bottom portion 36 of the plug 26, having an outer diameter about equal to the diameter of the vial rack holes 24, extends downwardly through and past the hole 24. This portion 36 of the plug 26 has a precision bored small hole 38 extending upwardly through the center thereof. It is this hole which determines and controls the rate of flow of fluid from the sample vials 28 such that the rate is predetermined and constant from vial to vial. Depending upon the desired resin-sample contact times, typical sizes through the hole are from 10 mils to 40 mils and typical suitable flow rates are from 4 cc/min to 20 cc/min.

The sample vial 28 is a wide mouth vial fitted with a cap 40 and a porous removable plug 42 which may be made, for example, of a plastic material or cotton. The lower end of the vial 28 tapers to a narrow neck 34 which when not capped for storage is inserted into the plug 26. At the beginning of the taper, the vial 28 is provided with a porous screen such as a wire mesh 44 which retains a loosely packed resin column 46 thereabove while allowing fluids to pass therethrough. During storage, and prior to adding sample, the vial 28 is fitted with a buffer solution which keeps the resin 46 moist.

The eluent vial rack 22 has a top member 48, a bottom member 50 spaced therefrom and side supports 52 and 54 spaced from the outer edges of the top and bottom members 48 and 50 so that the rack 22 can slide in and out of the slotted frame 10. The top and bottom members 48 and 50 of the eluent rack 22 are formed with a plurality of holes 56 which are aligned so that the centers thereof are directly below the centers of the plugs 26 of the sample rack 20. Eluent collector vials 58 are provided which are inserted into the holes 56 in the eluent rack 22. Means are provided to retain the collector vials 58 in the rack 22 when the rack 22 is removed from the apparatus. Here, a simple O-ring is shown to accomplish this. Alternatively, one can provide a ridge on the outer circumference of the vial itself or a rack having a bottom support on which the vials would rest.

The eluent vial rack is only required when one desires to collect the eluent and measure the radioactivity therein or otherwise use the eluent. However, if all measurements of radioactive uptake of the resin is performed on the resin itself, that is, on the sample vial 28, then there is no necessity of employing an eluent rack 22. In such an event the apparatus can include a front panel which extends from below the plugs 26 to the bottom member 18 and effectively seals the apparatus so that all fluids can be allowed to drain into the large reservoir below the plugs 26.

Another, and a preferred alternative, is the inclusion of a pump assembly 60 comprising a peristaltic pump which preferably has a precision adjustable flow rate. Such pumps are commercially available. A pump of this type can be used in conjunction with the flow rate control plug 26 or in place of the plug as the sole means for controlling the flow rate and hence resin-sample contact time. As shown in the drawings, a manifold type tubing 64 extends from the pump 62, through the side 12 of the frame 10 of the apparatus and connects to the individual plugs 26. The use of the pump increases the accuracy of the analysis by removing sample fluid which remains in the interstices of the resin particles and does not actually represent resin bound material.

In operation of the basic apparatus as originally set forth, the eluent vials 58 are placed in the eluent rack 22 and the rack 22 is slid into the frame 10 of the apparatus. The bottom caps (not shown) of the sample vials 28 are removed and the sample vials 28 are placed in the plugs in the sample rack 20 which has previously been slid into the frame 10. The caps 40 and plugs 42 are removed from the sample vials 28 and the buffer solution is allowed to drain out of the vials 28. The samples and reagents used in this procedure, as well as any control standards, should all be at room temperature. Prior to draining the buffer, the sample solution to be analyzed is prepared by dispensing 4.0 ml aliquots of radioactive reagent, such as about 0.25 uCi or less I125 labeled liothyronine in buffer solution, into individual mixing tubes using an accurate pipette. 0.1 ml of patient serum to be tested or control serum is added to the 4.0 ml of reagent. The serum-reagent sample solution is mixed well for several seconds and allowed to stand for five minutes to allow it to attain equilibrium. The buffer solution is then allowed to drain from the vials 28, as aforesaid. The serum-reagent sample solution or control solutions are then poured into the sample vials in a manner so as to cause storing of the loosely packed resin particles, thereby assuring maximum contact of resin and sample. When the serum-reagent mixture has passed through the column in the time as controlled by the plug and/or pump, it is preferable (but not necessary) to add a distilled water wash containing, for example, 4 ml of distilled water, to the column to remove all nonbound radioactivity. The wash solution is then allowed to drain. Thereafter, the vial is removed from the plug, the bottom cap preferably replaced and the vial is placed into a counting chamber. The total radioactivity is then counted and the $T_3$ binding ratio determined by the formula:

$$T_3 \text{ ratio} = \frac{\text{counts per minute (sample)}}{\text{counts per minute (control standard)}}$$

To obtain percentage resin uptake, multiple the $T_3$ ratio by 30. Generally, normal ranges (euthyroid) are ratios of from 0.83 to 1.17 or percentage uptakes of 25% to 35%.

The particular resin employed to form the column as well as the particular reagent does not form a part of this invention, since resins for this purpose are well-known. In general, the useful resins are ion exchange resins such as Amberlite IRA 400 manufactured by Rohm & Haas, Dowex 1×8 manufactured by Dow Chemical, or a synthetic resin such as Sephadex-G-25 manufactured by Pharmacia Fine Chemicals.

The above-described apparatus or the apparatus hereinafter described can be utilized with resin strips or sponges in place of resin columns, as previously described, and this alternative is contemplated as part of this invention.

The embodiment of the invention shown in FIGS. 2 and 3 is an automated apparatus utilizing a novel piston-cylinder vial type of arrangement as described in more detail below. The essential parts of this apparatus are sample vials 100 (the cylinder) into which the sample solution 102 is placed and resin tubes 104 (the piston or plunger) which contain the resin 106 preferably in the form of a loose column.

The sample vial 100 is a circular cylindrical open-mouthed tube, preferably having a flat closed bottom. The sample solution 102 containing a mixture of serum to be tested or control serum together with radioactive tracer solution is placed in the vial 100. The resin tube 104 is also a circular cylindrical tube. The outside diameter of the resin tube 104 is made slightly smaller than the inside diameter of the sample tube 100 so as to have a plunger-like fit therein. Resin tube 104 is open at both ends, the bottom end having a first porous screen 108 such as a wire mesh screen which supports the column of loose resin 106. The resin 106, as in the previous embodiment, is selected so as to have an affinity for the radioactive tracer material used. It should be understood that any material having an affinity for the tracer is suitable. The tube 104 preferably contains a second porous screen 110 which is well spaced from the top of the resin bed 106. The top portion of the resin tube 104 has an inwardly tapering wall 112 which is formed by a tubular extension 114 having an opening 116 at the end thereof. The tubular portion may be fit with a cap 118 to prevent dirt from entering the tube 104.

In operation wherein using the apparatus to test for $T_3$ utilizing radioactive $I^{125}T_3$, a 0.1 aliquot of serum is placed in the sample vial 100 together with a 4.0 ml of $I^{125}T_3$ reagent solution. The sample vial 100 is shaken and allowed to stand several minutes to insure equilibration of the $I^{125}T_3$ tracer with the TBG of the serum. The resin tube 104 is then inserted into the sample vial 100 causing the serum-reagent mixture to be force upward through the first mesh screen 108 and the resin 106 in a manner so as to create an agitation or swirling of the resin 106 in the serum-reagent solution 102. The fact that the second or top screen 110 is spaced about one-half inch from the top of the resin bed 106 so as not to pack the resin 106 but instead allow it to flow freely with the insurgent serum-reagent mixture 102, allows for greater surface area contact between the resin and the serum-reagent mixture 102 as has not previously been possible by other methods. This, of course, allows for more efficient binding of available tracer to the resin within the alloted contact time.

In fact, the resin-reagent contact in this procedure is threefold. Initially, the contact is obtained from the liquid 102 (serum-reagent) passing up through the bottom screen 108 and through the resin 104, carrying this resin 104 upwards and causing a fluid dynamic swirling motion. Secondly, as the resin 104 begins to settle, the resin beads again pass through the serum-reagent mixture allowing for further binding during this resin sedimentaiton phase. Thirdly, even further tagging is assured when the plunger (resin tube 106) is removed from the vial 100 causing the insurgent serum-reagent mixture 102 to vacate the plunger 104 and pass back through the settled resin 106 into the sample vial 100.

After withdrawal of the resin tube 104 from the sample vial 100, the serum-reagent eluent 102 is allowed to drain for a predetermined time into the sample vial 100, and at this point the contents of the sample vial 100 are placed in a counter for radioassay. Alternatively, one can place the resin tube 104 in a counter for radioassay. If desired, a wash step may also be introduced wherein the sample vial 100 is replaced with a second vial containing distilled water and the resin tube 104 inserted into this second tube to effect final removal of tracer material which was not bound to the resin. This wash solution can be combined with the sample solution for assay purposes.

It is a further aspect of this concept to introduce a mechanical device which will provide for simultaneous multiple tests to be performed without any further technician involvement after the initial setup preparations except for the step of radioassay. This device provides, as previously stated, the means for performing multiple tests, and less technician manipulations which will reduce chances of errors due to technician fatigue, effects of repetition, and other variables which can become the source of inconsistency and erroneous results. Prior to this device and methodology, many procedural steps such as wash and rinse steps, addition of reagents, timing, and so on, could lead to spillage, contamination, and destroyed tests leading to time consuming retesting.

The apparatus shown in FIGS. 2 and 3 comprises a housing 120 which acts as the base of the apparatus. The housing contains mounted therein the necessary circuit elements, control knobs, switches, indicator lamps, and mechanical drive members used in connection with operation of the apparatus. Mounted to the housing 120 from the inside thereof and extending vertically therefrom are four cylindrical support posts and guides 122 spaced from and opposite each other. Two posts 122 are toward the front of the base 120 and two posts are toward the back of the base 120.

Mounted near the top of the posts 120 is a resin tube rack support means consisting of two side members 124 and 126 fastened to each of two side posts, one fastened to the posts on the left side of the apparatus and the other fastened to the posts on the right side of the apparatus. These side members are fastened to the posts by means of set screws (not shown) which extend inwardly to the posts 122 which extend vertically through holes in the side members 124 and 126 provided to fit the posts 122 therethrough. The inner sides of the side members are provided with a horizontally extending slot 128 and 130, respectively, along which the resin tube rack 132 is slidably supported. Lying over the side members 124 and 126 is a dust cover 134. The dust cover 134 is provided with holes positioned such that the four posts fit therethrough.

The resin tube rack 132 comprises a rectangular flat top member 136 having a thickness and width such that it can slide into the slots 128 and 130 in the side members 124 and 126. Spaced from the top member 136 and separated therefrom by two side supports 138 and 140 is a rectangular, flat bottom member 142. The bottom member 142 which is affixed to the side supports 138 and 140 is of the same depth as the top member 136 but is not as wide as the top member 136. Top and bottom members 136 and 142 are each provided with a plurality of holes 144 preferably in the form of several rows. The centers of the holes of the top member 136 lie directly above the center of the holes of the bottom member 142. The diameter of the holes of the bottom member are about equal to the outer diameter of the body of the resin tube 104 while the holes in the top member are of a diameter about equal to the top portion 114 of the resin tube 104 so that the resin tube fits snugly but easily into the holes. Means are provided for retaining the resin tube 104 in position in the resin tube rack 132. Alternate means are shown in FIG. 2. For example, the second tube from the left is shown to have two O-rings 145 and 146, one at the lower surface of the bottom member 142 and one at the top surface of the top member 136. The tube on the left and the tubes shown in FIG. 3 are shown to have a small ridge 148 extending around its circumference which snaps into a small depression 150 around the central portion of the surface forming the holes of the top member 136. On the bottom member of the resin rack 132 there is mounted a micro-switch 133 which is activated when the resin tube 104 and sample vial 100 are in the position where the tube 104 has been inserted into vial 100 to its furthermost extent.

The base 120 of the apparatus is provided with a large opening 152 through which a tubular member 154 having a threaded inner surface and a flanged top surface can move up and down. The tubular portion extends vertically downward into the housing and is threaded onto a shaft 156 which is attached to a reversible motor 158. The motor 158 is mounted to the housing 120. Turning of the motor causes raising or lowering of the tubing 154. The flanged part of the tubing 154 is screw mounted onto a movable platform 160 which in turn supports a removable sample rack 162.

The sample rack 162 comprises a top member 164 separated from a bottom member 166 by side supports 168 and 170. The top member 164 is provided with a plurality of holes which align under the holes in the resin rack 132 when the sample rack 162 is positioned in the apparatus. The holes are of a diameter so as to snugly allow the sample vials 100 to pass therethrough. The bottom member 166 of the sample rack 162 has a plurality of depressions 172 in its upper surface in which the bottoms of the sample vials 100 rest. The sample rack 162 is slidably supported in the apparatus by means of slots 174 and 176 in a pair of bottom movable support members 178 and 180, respectively. These bottom movable supports 178 and 180 travel along guide posts 122 onto which they are placed by means of holes through the supports 178 and 180. The top of the housing 120 is provided with a small opening 182 through which a second microswitch 184 extends. The microswitch which is mounted to the housing is activated when the platform is in its lowest position. In this position, both the sample rack 162 and the resin rack 132 can be removed from the apparatus without interference or contact of sample vials 100 with resin tube 104.

For convenience, the apparatus is provided with a master ON-OFF switch 186, a master switch indicator light 188 connected to indicate when the master switch is in the ON position, a rheostate 190 to control the speed of the motor 158, a time delay control 192 which controls the contact time of resin and sample solution, an annunciator panel 194 to indicate the cycle position of the apparatus, and an activator switch 196 to activate the cycling. Prior to operation and during storage, the apparatus is maintained in the position where the platform is in a raised position so that the resin tubes 104 are inserted in the sample vial 100 which contain a buffer solution. When ready for operation, the motor is activated to lower the platform and the buffer solution is allowed to drain from the resin 106. The sample rack 162 is removed and sample vials containing controls and sample solutions 102 are inserted in the rack 162. The sample rack 162 is slid into position in the apparatus and the apparatus is activated for cycling. During the first part of the cycle, the motor goes in reverse, raising the platform and sample vial rack by unscrewing the tube 154 on the motor shaft 156. When the platform is raised to its maximum height as adjusted by microswitch 133 activating screw 198, which is screwed into the top of the sample rack 162 opposite the microswitch 133, the motor stops and the contact-time delay means is activated for a predetermined time. After the elapse of this predetermined time period, the motor 158 is caused to rotate in a forward or clockwise manner causing the platform 160 to descend until the bottom of the platform 160 rests near or on the top of the housing 120 and the second microswitch 184 is activated causing the motor 158 to stop and ending the cycling until the restart switch 196 again activates the apparatus.

It should be understood that other means for activating and cycling can be provided and that it is possible to automatically provide a resin wash cycle following the previously described cycle. For example, if the first row contained sample and the second row distilled water wash and so on, after the resin-sample contact cycle, one could manually shift one of the racks the equivalent of one row and restart the cycling, thereby adding a wash step, or one could provide automatic means to achieve this function.

Figure 4:
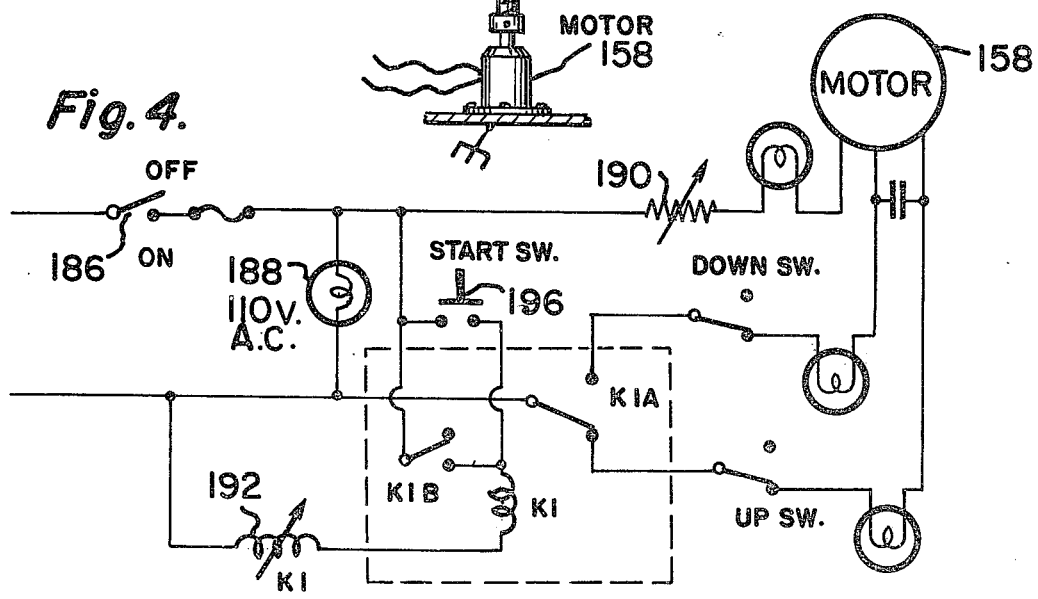
FIG. 4 is a circuit diagram for operation of the apparatus of FIG. 2.

FIG. 4 is a circuit diagram showing a circuit suitable for operating the apparatus. It should be understood that many other circuits can be employed for operating the device and such circuits are well-known in the art. In fact, such circuits as are commercially employed for use as garage door openers can be adapted for use in the novel apparatus. The circuit as shown includes the ON/OFF toggle switch 186, one side of which is connected to one leg of an AC power source and the other side of which is connected through a fuse 191 to a means 190 for varying the motor speed. The means shown for varying the motor speed is a variable resistor 190. Alternatively, one can use other means known in the art as a silicon control rectifier. The other side of the variable resistor is connected to the commutator of the motor 158 through one of the anunciator lights. The lead between the fuse 191 and the variable resistor 190 is also connected to one side of the normally open push button start switch 196 and to one side of a switching contact of a relay K. The relay K is a double pole, double throw time delay having two switching contacts and an inductor coil for affecting the time delay. The second leg of the AC power source is coupled to means 192 for changing the time delay of the relay, which means is shown herein as a variable inductor serially connected to the inductor of the relay. Alternatively, means 192 can be, for example, a variable capacitor. The second leg of the AC power supply is also connected to the second of the switching contacts K1A of the relay K. The other side of the switching contact K1A, when in one position, is coupled to switch 133 which causes the motor to turn in a reverse direction thereby causing the platform to be lowered, or when in its other position, is connected to switch 184, which when activated, causes the motor to operate in a forward direction and causes the platform to be raised. The other side of the switches 133 and 184, respectively, are connected to the motor in a manner so as to cause the motor to operate in either a reverse or forward direction, respectively.

We claim:

1. A method for determining, in multiple samples, an index of a constituent of body fluid utilizing radioactive tracers comprising the steps of:
   (a) adding the same known quantity of a radioactive tracer to each aliquot of sample of body fluid to be measured;
   (b) mixing each radioactive tracer-sample aliquot to attain uniformly equilibrated solutions;
   (c) placing a plurality of vials containing a loosely packed resin column therein, which column is supported on a porous member, into a vial rack adapted to hold said vials;
   (d) adding said equilibrated solutions to said vials in a manner as to cause agitation of said resin;
   (e) automatically controlling the contact time of said equilibrated solutions with said resin to a predetermined time of between 10 seconds to 2 minutes by way of contact time control means associated with said vial rack;
   (f) determining the amount of radioactivity by the resin in each vial; and
   (g) comparing said amount of found radioactivity with control standards to obtain a quantitative result.

2. The method recited in claim 1, wherein said sample of body fluid is blood serum, and wherein said radioactive tracer is a radioactive iodine solution.

3. The method recited in claim 2, wherein said radioactive tracer is $I^{125}$ labeled liothyronine in a buffer solution.

4. A method for determining an index of a constituent of body fluid utilizing radioactive tracers comprises:
   (a) placing an aliquot of a sample to be measured in a first cylindrical flat bottom tube;
   (b) adding a known quantity of radioactive tracer to said sample and allowing the mixture to equilibrate;
   (c) adding resin in the form of a loosely packed column to a second cyclindrical tube having a flat porous bottom member through which fluid can flow and which supports said resin, said first tube having an inside diameter such that said second tube fits therein in a plunger-like manner;
   (d) pushing said second tube to the bottom of said furst tube thereby forcing said equilibrated mixture through said porous bottom member of said second tube causing agitation and contact of said resin by said equilibrated mixture;
   (e) withdrawing said second tube from said first tube in a predetermined period of time thereby allowing unbound tracer of said equilibrated mixture to drain from said resin back into said first tube; and
   (f) determining the amount of tracer bound by said resin.

5. An apparatus useful for the analysis of multiple samples of body fluid comprising:
   (a) a vial rack for holding a plurality of vials said rack including a vertical frame which supports a horizontal member, said horizontal member having means for supporting said vials therein;
   (b) a plurality of vials having a wide open upper end and a narrow open lower end, said vials having a porous member mounted therein at or near its lower end for supporting a loosely packed resin column;
   (c) a plurality of precision bore plugs for automatically controlling the contact time of sample solutions with resin in said vials to a predetermined time which is equal for all samples and is substantially less than saturation time, said plugs being mounted in holes provided therefore in said horizontal member of said vial rack and having a wide bore opening in the upper half of said plug adapted to accept and hold the narrow bottom portion of said vials and a narrow precision bore extending from said wide bore to the bottom of said plug.

6. The apparatus recited in claim 5 wherein said narrow precision bore is from 10–40 mils in diameter.

7. An apparatus useful for the analysis of multiple samples of body fluid comprising:
   (a) a vial rack for holding a plurality of vials said rack including a vertical frame which supports a horizontal member, said horizontal member having means for supporting said vials therein;
   (b) a plurality of vials having a wide open upper end and a narrow open lower end, said vials having a porous member mounted therein at or near its lower end for supporting a loosely packed resin column;
   (c) means for automatically controlling the contact time of sample solution with resin including a time flow variable peristaltic pump and tube means for attaching the bottom of each vial to said pump.

8. An apparatus useful for the analysis of body fluid comprising:
   (a) a resin tube containing resin therein, said resin tube having an open wide-mouthed flat bottom provided with a porous screen thereon;
   (b) a sample vial for containing sample solution, said sample vial having a flat close bottom, the outer dimensions of said resin vial being such as to fit into the inside of said sample vial in a plunger-like manner so as to cause sample solution within said sample vial to flow up and into said resin tube through said porous screen and mix with said resin;

(c) means for extracting said resin tube from said sample vial in a predetermined period of time so as to allow said sample to drain from said resin tube back into said sample vial.

9. The apparatus recited in claim 8, including means for supporting said resin vials in said vial rack and including a sample vial rack having means for supporting said sample vials, both vial racks being slidably supported in said apparatus, said sample vial rack being in alignment with said resin vial rack such that when said sample vial rack is raised in the apparatus, said resin tubes fit within said sample vials, said apparatus includes means for causing said sample vials to move upwardly so as to cause said resin tubes to fit therein.

* * * * *